United States Patent
Tsang et al.

(10) Patent No.: US 6,475,747 B2
(45) Date of Patent: *Nov. 5, 2002

(54) METHOD FOR DETECTING *CRYPTOSPORIDIUM PARVUM* OOCYSTS

(75) Inventors: Victor C. W. Tsang, Decatur; Yeuk-Mui Lee, Doraville; Patrick W. Johnson, Decatur; Michael J. Arrowood, Duluth; Jeffrey L. Call, Tucker, all of GA (US)

(73) Assignees: The United States of America as represented by the Department of Health and Human Services, Washington, DC (US); Centers for Disease Control and Prevention, Atlanta, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/958,945

(22) Filed: Oct. 28, 1997

(65) Prior Publication Data

US 2001/0049116 A1 Dec. 6, 2001

(51) Int. Cl.$^7$ ............... G01N 33/53; G01N 33/569; G01N 33/543; G01N 33/536
(52) U.S. Cl. ............. 435/7.22; 435/7.7; 435/7.92; 436/536; 436/541
(58) Field of Search ............. 435/7.1, 7.22, 435/7.7, 7.92; 436/514, 536, 541

(56) References Cited

U.S. PATENT DOCUMENTS 6,146,838 A * 11/2000 Williams et al. ............. 435/7.2

FOREIGN PATENT DOCUMENTS

| WO | WO 93/24649 | 12/1993 |
|----|-------------|---------|
| WO | WO 97/08204 | 3/1997 |
| WO | WO 98/41867 | 9/1998 |
| WO | WO 98/52974 | 11/1998 |

OTHER PUBLICATIONS

Aveldano et al., J of Neurochem., 57:250–57, 1991.*
Byers et al., J. Biol. Chem., 262(19):9166–74, 1987.*
Lumb et al., Immunol. Cell Biol., 67:267–70, 1989.*
Garcia et al., J. of Clin Microbiol., 25(1):119–21, 1987.*
Smith et al., Water Science & Technology, 24(2):169–72, 1990.*
Jackson et al., J. of Immunol. Methods 190(2):189–97, 1989.*
Harlow & Lane, Cold Spring Harbor Labs, p. 579, 1988.*
Rochelle et al., Applied Envir. Microbiology 63: 2029–2037, May 1997.*
Musial et al., Applied Envir. Microbiology 53:687–692, 1987.*
Tatalick et al., Vet.Parasitology 58: 281–290, 1995.*
Stinear et al., Applied Envir. Microbiology 62:3385–3390, 1996.*
Sigma Chemical Company: Biochemicals, Organic Compounds for Research and Diagnostic Reagents, pp. 54 and 915, 1994.*
Uhl et al., Infection and Immunity 60: 1703–1706, 1992.*
Okhuysen et al., Infection and Immunity 62: 4667–4670, 1994.*
"Hydrophobic and Electrostatic Cell Surface Properties of *Cryptosporidium parvum*", C. Drozd and J. Schwartzbrod, *Applied and Environmental Microbiolgy*, Apr. 1996, vol. 62, No. 4, pp. 1227–1232.
"An Evaluation of Methods for the Simultaneous Detection of Cryptosporidium Oocysts and Giardia Cysts from Water", K.M. Shepherd and A.P. Wyn–Jones, *Applied and Environmental Microbiology*, Apr. 1996, vol. 62, No. 4, pp. 1317–1322.
"Factors Influencing Cryptosporidium Testing in Connecticut", Christine L. Roberts et al., *Journal of Clinical Microbiolgy*, Sep. 1996, vol. 34, No. 9, pp. 2292–2293.

* cited by examiner

*Primary Examiner*—Gary L. Kunz
*Assistant Examiner*—Sharon L Turner
(74) *Attorney, Agent, or Firm*—Klarquist Sparkman, LLP

(57) ABSTRACT

Methods for detecting parasites, such as *Cryptosporidium parvum*, in turbid and non-turbid samples by solubilizing molecular markers or antigens of the parasite. The molecular markers are solubilized by incubating a sample containing the parasite with a solubilization buffer and detecting the solubilized antigens by electrochemiluminescence. The solubilization buffer contains one or more detergents alone or in combination with one or more denaturing agents in a buffered solution. The methods are an improvement over existing immunofluorescence assays for *C. parvum* because the methods described herein are quantitative, reproducible, have high sensitivity, are not labor-intensive, require only minimal sample processing, and avoid being adversely affected by sample turbidity. In addition, by using a electrochemiluminescence assay, microscopy is not required.

28 Claims, 2 Drawing Sheets

METHOD FOR DETECTING *CRYPTOSPORIDIUM PARVUM* OOCYSTS

This invention was made in the Centers for Disease Control. Therefore, the United States Government has certain rights in this invention.

FIELD OF THE INVENTION

The present invention relates to the field of detection assays and more particularly to an improved method for detecting *Cryptosporidium parvum* oocysts.

BACKGROUND OF THE INVENTION

Parasitic infections of the gastrointestinal tract are prevalent around the world. Many gastrointestinal parasites are transmitted by the consumption of contaminated food or water. Although gastrointestinal parasitic infections in the general population cause abdominal disorders for only a short period of time, in the immunocompromised individual, a parasitic infection can be deadly.

*Cryptosporidium parvum* (*C. parvum*) is a food or water-borne parasite that infects humans and animals causing severe intestinal distress. Since the 1970's, *C. parvum* has been receiving increased world wide attention. In the early 1980's following two outbreaks of *C. parvum* infections in the United Kingdom resulting in a total of 516 cases, the British government was compelled to devise a method for detecting *C. parvum* in water. (K. M. Shepherd et al., APPLD. AND ENVIRON. MICRO., Vol. 62, No. 4 pp. 1317–1322 (1996)). In the United States, waterborne outbreaks of *C. parvum* are being reported with increasing frequency. One of the latest outbreaks took place in Milwaukee, Wis. in April 1993 involving the infection of an estimated 400,000 people. (C. Drozd et al. APPLD. AND ENVIRON. MICRO., Vol. 62, No. 4 pp. 1227–1232 (1996)). Infection caused by *C. parvum* is particularly dangerous because it can cause prolonged diarrheal illness that may be potentially fatal for immunocompromised individuals.

*C. parvum* is a parasite that infects its host by invading the intestinal and urogenital systems. *C. parvum* organisms may be transmitted in a variety of ways including via contaminated food or water, animal to animal contact, via farm animals such as sheep and calves, or alternatively by oocysts in feces. Human infections generally result from zoonotic spread, person-to-person contact, fecal-oral contact, oral-anal contact or waterborne transmission. Although, cryptosporidiosis occurs worldwide, children, travelers to foreign countries, male homosexuals, and medical personnel caring for patients with the disease, are at particular risk. In developed countries, 1 to 4% of children with gastroenteritis harbor *C. parvum* oocysts; and in developing countries, 4 to 11% of such children have cryptosporidiosis. Apart from humans, Cryptosporidium infections are widespread in several other vertebrates such as mammals, reptiles and fish: and accordingly, the frequency of cryptosporidiosis is reported to be relatively high for animal handlers and veterinarian personnel.

Unlike other coccidia, *C. parvum* is found on the brush border of intestinal epithelium and not within deep intracellular regions. Typically, *C. parvum* organisms are small (2 to 6 $\mu$m) spherules that inhabit the microvillus border of the intestinal epithelium arranged in rows along the brush border of the jejunum. After introduction into the intestine, *C. parvum* sporozoites attach to the microvilli surfaces and reproduce by schizogony (asexually). The resulting infective oocysts are passed into the intestinal lumen and passed in the feces. Following ingestion of the oocysts by another vertebrate, the oocysts release sporozoites that attach themselves to the epithelial surface and initiate a new cycle of infection.

As *C. parvum* organisms invade the surface of intestinal cells, the host experiences symptoms such as reduced appetite, severe diarrhea and chronic fluid loss. In normal hosts, the onset of the disease is explosive, with profuse, watery diarrhea and abdominal cramping that lasts from 4 to 14 days following exposure. The symptoms generally persist for 5 to 11 days, and then rapidly abate as remission of the parasite occurs in about 10–15 days. However, in immunocompromised individuals, (i.e. marasmic and malnourished children, individuals with congenital hypogammaglobulinemia, those receiving immunosuppressants for cancer therapy or organ transplantation, and patients with AIDS), onset of the disease is more gradual and diarrhea is more severe, with daily fluid losses of up to 15 to 20 liters. Unless the underlying immunologic defect is corrected, the diarrhea may continue persistently or remittently for life. (Merck Manual, Chapter 15 p. 237 16th ed. (1992)).

There is no effective, specific anti-*C. parvum* therapy available at present. Although some patients have responded positively to therapy with conventional antibiotics such as spiramycin and paromomycin, the result of infection is frequently fatal for immunocompromised individuals. In fact, cryptosporidiosis is one of the predominant causes of death in immunocompromised patients.

In light of the potential disastrous consequences of *C. parvum* infection, sensitive, efficient methods for detecting *C. parvum* contamination are necessary. In humans, the typical source of cryptosporidiosis is contaminated water, therefore safeguarding water supplies is a primary goal. The United States Environmental Protection Agency has recognized the necessity for improved detection methods by initiating the establishment of mandatory guidelines for *C. parvum* levels in drinking water.

Currently available detection systems indicate that *C. parvum* organisms are observed in "spikes"; meaning that levels of *C. parvum* in samples collected upstream and downstream, from the same source of the contamination, may not be identical when simultaneous readings are made. Consequently, *C. parvum* levels recorded from one location may differ significantly from readings taken from the same location minutes later. Detection of *C. parvum* in water is further complicated because the initial source of infection is difficult to identify. An abnormally high *C. parvum* concentration may be caused by water run-off from contaminated farm or pasture land, or an infant's soiled diaper carelessly discarded into a stream.

Ideally, continuous filtration systems having the capability to capture and retain *C. parvum* organisms for subsequent analysis would be installed in all water supply reservoirs to allow for continuous monitoring. Unfortunately, filtration systems currently in use often have filtration cartridges that either fail to retain organisms, frequently become clogged with mud or sediment, or must be replaced or cleaned with a frequency that renders the cartridges impractical.

*C. parvum* detection assays presently in use are cumbersome and frequently inaccurate. For example, most assay test samples begin as crude mixtures of *C. parvum* oocysts separated out from mud deposits collected by filters. The oocysts are isolated by processes involving centrifugation and ultrafiltration. Separating oocysts in this manner is often tedious and inefficient since each time the test sample is spun and filtered, oocysts are lost in the process, inevitably resulting in lack of sensitivity and related inaccuracies. Another significant disadvantage of such assays is the large amount of time required for processing test samples. For example, in order to improve the optical properties of test samples for detection, oocysts must be stained. Typically, staining and subsequent detection procedures can take up to four days. Furthermore, samples can be tested only in small increments (i.e. 50 μl), and the sensitivity of most currently available assays is very low. Generally at least 50,000 *C. parvum* oocysts per milliliter must be present for a positive detection result. Therefore, *C. parvum* assays currently in use are generally inefficient, inaccurate and inconsistent.

Another barrier to effective Cryptosporidium screening concerns sample turbidity. The term "turbidity" refers specifically to the clarity or transparency of water and the effect that any suspended particles in the water may have on this clarity. Turbidity is determined by quantifying the amount of light allowed to pass through a sample and is measured in NTUs (nephelometric turbidity units). Many source water sites of public water reservoirs, e.g. rivers and lakes, often have turbidities up to 100 NTU, whereas finished water, e.g. reservoirs for public consumption, tend to have turbidities in the range of 0 to 5 NTU.

Because it is commonly suspected that Cryptosporidium contamination occurs at source water sites, efforts have been focused on assaying samples at reservoir intakes. Several gallons of source water are pumped through filters that are rated to capture particles the size of oocysts or larger. Pumping source water in this way causes large amounts of sediment to obstruct the flow of water through filters and therefore limit the volume of water passing through the filters. The filter retentates are then eluted and assayed for the presence of microorganisms. These retentates can have turbidities up to 300,000 NTU and yield highly variable *C. parvum* oocyst counts by immunofluorescence assay due to the loss of oocysts that occurs in multi-step sample processing.

Oocysts present in filter eluate often tend to be washed away during processing and therefore go undetected in the final step of detection assays. Consequently, currently available methods such as immunofluorescence assays (IFA) and enzyme immunoassays (EIA), are mainly useful for detecting oocysts in "clean" samples, i.e. samples that have low turbidity. Such assays are more likely to give reproducible results with clean samples than those that are considered "dirty", i.e. samples that have high turbidity.

Clinical diagnosis of cryptosporidiosis is made by recovering acid-fast oocysts from stool samples. Excretion of acid-fast oocysts is most intense during the first four days of illness but persists for the duration of diarrhea. Other assays currently in use for diagnostic purposes involve the use of formalin-ethyl acetate sedimentation or Sheather's sugar flotation stool concentration procedure to enhance the yield of oocysts in specimens containing few oocysts. Commercial fluorescein-labeled monoclonal antibody kits also provide detection of oocysts in clinical specimens. (Merck Manual, Chapter 15 p. 237 16th ed. (1992)). The disadvantage of such clinical tests is that depending on the stage of *C. parvum* infection, the assays may or may not be adequately sensitive for detecting oocysts. In addition, such clinical tests generally involve a multitude of steps thereby introducing a greater likelihood of inaccuracies. Furthermore, no "standard" for testing stool specimens for *C. parvum* has been established, and so the absolute sensitivity of currently used methods has not been assessed. (Christine L. Roberts et al., JOURN. OF CLIN. MICRO., Vol. 34 No. 9, pp. 2292–2293 (1996)). Other problems associated with *C. parvum* testing include extensive processing time and low test positivity rates.

In summary, existing assays for parasites such as *C. parvum* are irreproducible, insensitive, labor-intensive, susceptible to interference by sample turbidity, and time consuming. In addition, existing assays are not quantitative, and scientific data correlating parasite levels in drinking water with incidence and severity of disease in healthy and immunocompromised persons, are unavailable. Useful assays that enable correlation of disease-parasite levels are required for the development of environmental guidelines for safeguarding water sources against *C. parvum* and other parasitic infestation. What is needed therefore, is a sensitive, quantitative and reproducible assay for food or waterborne parasites that can efficiently process numerous samples without requiring a multitude of steps and subjective determinations.

SUMMARY OF THE INVENTION

An efficient and sensitive method for the detection of food or waterborne parasites, such as *C. parvum* oocysts, is provided. In accordance with the method, molecular markers of the parasite are solubilized, thereby allowing recognition and detection of the parasite in turbid samples. Unlike prior art assays, the results of the assay described herein are both reproducible and quantitative. In addition the assay is especially useful for detecting *C. parvum* oocysts present in source water such as recreational water and natural bodies of water, finished water such as community water reservoirs, biological fluid samples, or fecal samples, without interference from sample turbidity. The assay is highly sensitive, allowing for the detection of less than 50,000 oocysts per milliliter, and permits rapid sample testing.

The assay described herein includes the steps of solubilizing molecular markers, or antigens, of the parasite and detecting the antigens by immunological means. Preferably the assay is useful for detecting *C. parvum* in test samples by solubilizing oocyst antigens and detecting the solubilized antigen, preferably by magnetic matrix capture and electrochemiluminescence. The assay is particularly suited for parasite detection in environmental water, biological fluid samples, and fecal samples because it can operate in both low and high turbidity samples, has high reproducibility, and can be performed with little sample manipulation or processing.

Accordingly, it is an object of the present invention to provide a qualitative or quantitative assay for the detection of food or waterborne parasites such as *C. parvum* oocysts.

It is another object of the present invention to provide a detection assay for parasites, such as *C. parvum* oocysts, in either source or finished water.

It is yet another object of the present invention to provide a detection assay for parasites, such as *C. parvum* oocysts, in turbid samples, particularly turbid water samples.

It is another object of the present invention to provide a detection assay for food or waterborne parasites, such as *C. parvum* oocysts, in biological samples such as biological fluid samples and stool, or fecal samples.

Another object of the present invention is to provide a quantitative detection assay enabling the correlation of parasite levels in the food or water source, such as *C. parvum* oocyst levels in drinking water, and the incidence of disease in normal, healthy individuals, or immunocompromised individuals.

Yet another object of the present invention is to provide a method for solubilizing molecular markers of parasites, such as *C. parvum* oocysts.

Another object of the present invention is to provide a kit for an optimized assay configuration for automated point-of-use analysis for detecting parasites, such as C. parvum, in water, biological fluids, or fecal samples.

Another object of the present invention is to provide a method for the immunological detection of parasites, such as C. parvum oocysts, that utilizes electrochemiluminescence technology.

These and other objects, features and advantages of the present invention will become apparent after a review of the following detailed description of the disclosed embodiments and the appended claims.

DETAILED DESCRIPTION

Figure 1:
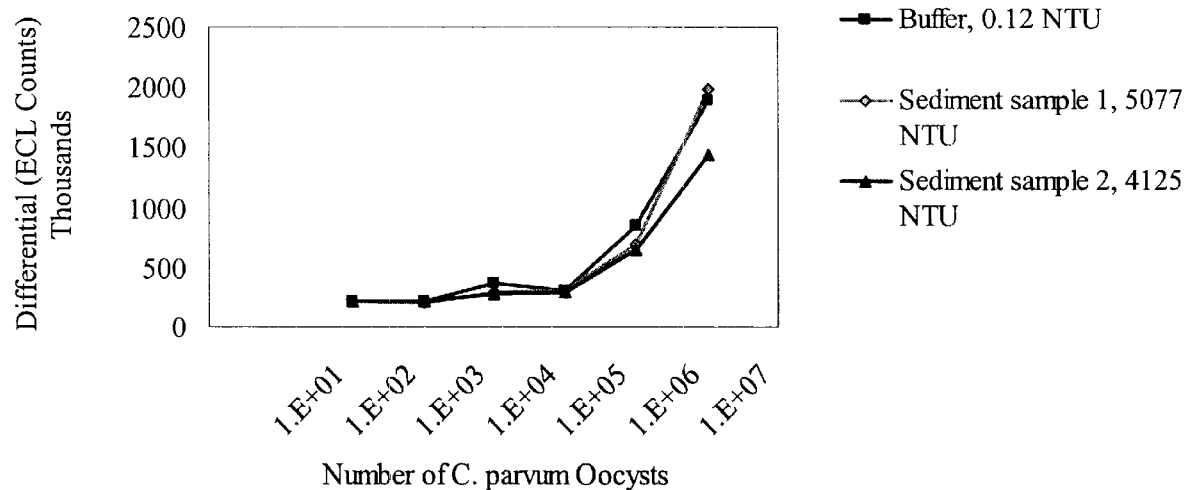
FIG. 1 is a graph showing titration curves, measured by electrochemiluminescent counts, of C. parvum oocysts in buffer or sediment samples having various nephelometric turbidity unit (NTU) values.
Figure 2:
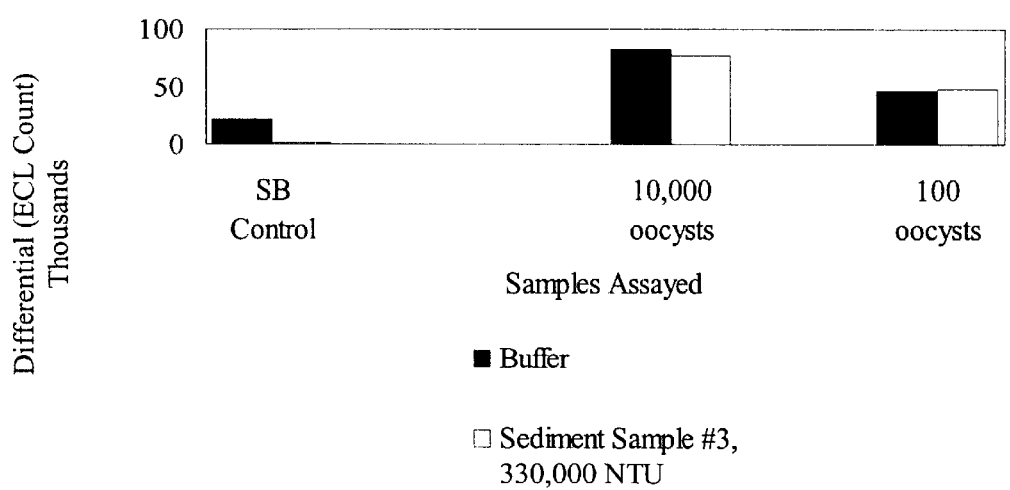
FIG. 2 is a bar graph showing a comparison of oocyst detection, measured as electrochemiluminescent counts per sample, in buffer versus sediment samples. The graph demonstrates that sediment samples with up to 330,000 NTU can be assayed using the method described herein for the presence of OW3 antigens in spiked samples.
Figure 3:
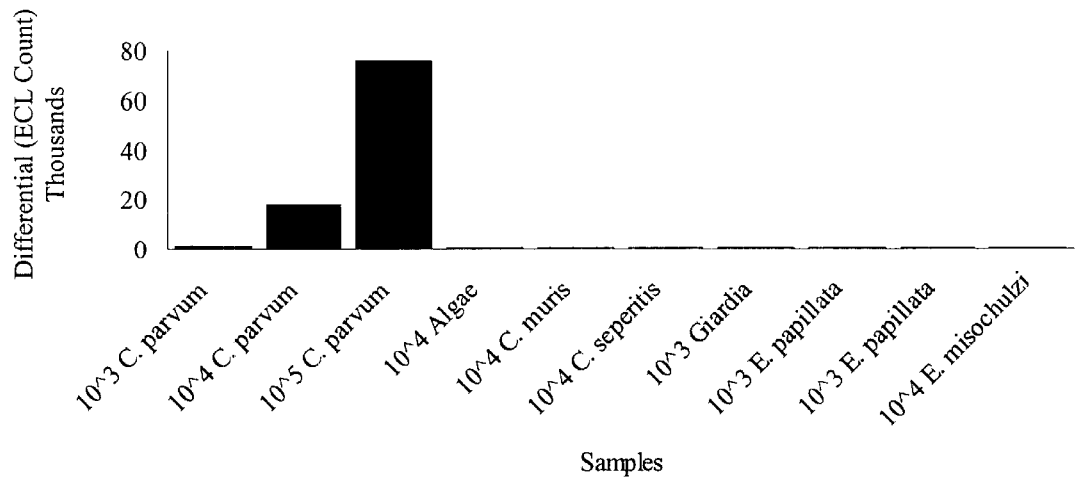
FIG. 3 is a bar graph showing electrochemiluminescent counts for nine different parasites, measured using the detection assay described herein with a monoclonal antibody specific for C. parvum.
Figure 4:
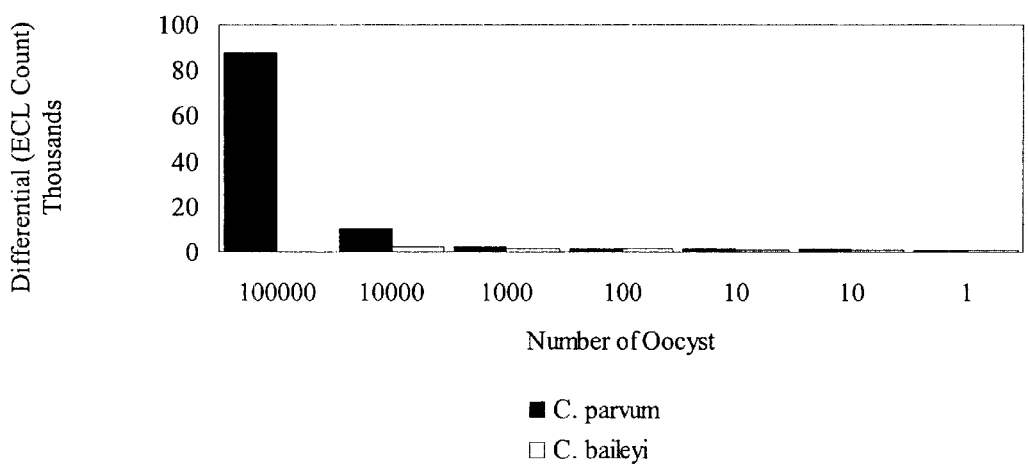
FIG. 4 is a bar graph of differential electrochemiluminescent counts for C. parvum and a related species, C. baileyi, demonstrating that the detection assay described herein is specific for C. parvum and does not cross-react with Cryptosporidium baileyi.

A method or assay for the detection of food or waterborne parasites is provided. The method is useful for the detection of parasites in a variety of samples including, but not limited to, source water such as recreational water and natural bodies of water, finished water such as community water reservoirs, biological fluid samples, fecal samples, and other turbid samples without interference from sample turbidity. The assay permits rapid sample testing and is highly sensitive, allowing the detection of less than 50,000 oocysts of the parasite per milliliter. Preferably, the assay is capable of detecting oocysts at a concentration as low as 10,000 oocysts per milliliter, most preferably as low as 1,000 oocysts per milliliter.

In accordance with the method provided herein, molecular markers of the parasite are solubilized and the solubilized molecular markers are detected with an immunologic assay, preferably utilizing electrochemiluminescence. The method is particularly advantageous because microscopy is not required and the results lack susceptibility to influence by turbidity. In addition, the results are both quantitative and reproducible.

The term "molecular marker" is defined herein as an antigen of the parasite. Preferably, the antigen is a membrane-bound protein or glycoprotein. Most preferably the antigen is unique to the parasite being detected by the assay and is found on the surface of an oocyst of the parasite.

Preferably, the assay detects parasites such as Plasmodium (particularly *Plasmodium falciparum*), Trypansoma (particularly *Trypansoma cruzi*), Cyclospora, Giardia, and Cryptosporidium. More preferably, the assay detects *Cryptosporidium parvum* (*C. parvum*). Most preferably, the assay detects solubilized antigens or molecular markers of C. parvum oocysts.

Molecular Marker Solubilization

One or more molecular markers of the parasite to be detected in a sample, such as membrane-bound proteins or glycoproteins of the oocyst stage of the C. parvum organism, are solubilized by combining a sample containing the parasite with a solubilization buffer for a sufficient amount of time and under conditions that facilitate protein solubilization without resulting in protein denaturation to the extent that it would impair the formation of an antibody-antigen complex between the solubilized molecular marker and an antibody having specificity for the molecular marker.

The solubilization buffer is a buffered solution containing one or more detergents alone or in combination with one or more denaturing agents. Preferably, the solubilization buffer for C. parvum oocyst antigens contains a detergent in a mildly alkaline buffer solution.

In general, membrane-bound proteins or glycoproteins present on the surface or outer wall of the parasite, preferably the oocyst stage of the parasite, are solubilized using a wide range of detergents, denaturing agents, or a combination of detergents and denaturing agents, in a buffered solution. Exemplary detergents and denaturing agents include, but are not limited to, Zwittergent™ detergent, Tween-20™ detergent, Triton X-100™ detergent, NP40™ detergent, urea, sodium dodecyl sulfate, guanidine hydrochloride. The preferred pH is mildly acidic or mildly alkaline. The term mildly acidic is defined herein as less than pH 7 and greater than pH 4. The term mildly alkaline is defined herein as greater than pH 7 and less than pH 10. The optimal formulation of solubilization buffer depends on the physicochemical properties of the molecular marker to be solubilized and detected by the detection assay.

For example, in a preferred assay, the antigen to be detected is the target epitope of OW3, which is found on the C. parvum oocyst cell wall and is currently the desired molecular marker for C. parvum detection in some of the available immunofluorescence assays (IFA). In a preferred embodiment of the detection method described herein, OW3 antigens are solubilized with a solubilization buffer containing Zwittergent™ detergent and Tris-HCl, at alkaline pH, at a temperature above room temperature for at least 30 minutes. More preferably, C. parvum OW3 antigens are solubilized with a solubilization buffer containing less than 1% Zwittergent™ 3–10 detergent and less than 0.1 M Tris-HCl (pH 8–10) at a temperature greater than 75° C. for between 30 and 90 minutes. Most preferably, C. parvum OW3 antigens or epitopes are solubilized with a solubilization buffer containing approximately 0.65% Zwittergent™ 3–10 and approximately 0.05M Tris-HCl, approximately pH 8.0, at approximately 95° C., for approximately one hour.

The solubilization of the molecular markers, or surface antigens, of other parasites or oocysts of parasites, can be determined by those skilled in the art by spiking a sample with a known amount of parasite to be detected; adjusting the choice and concentration of detergent and denaturing agent, pH, temperature, length of incubation, and degree of agitation; and maximizing the conditions that yield the highest concentration of solubilized, or detectable, antigen by immunoassay.

Antigen Capture and Detection

Following solubilization, the solubilized marker or markers are reacted with one or more antibodies that bind to the solubilized antigen under conditions that facilitate antibody-antigen complex formation. The antibodies may be monoclonal or polyclonal antibodies. Most preferably, the antibodies are monoclonal antibodies specific for the solubilized antigen. The antibodies are prepared in accordance with methods known to those skilled in the art. The molecular markers function as representatives of the organism being detected by the assay.

For example, epitopes of OW3 are representative of *C. parvum*. OW3 is particularly selected because the epitopes of OW3 are present in abundance on the *C. parvum* oocyst wall, but not on other Cryptosporidium species or other parasites.

Preferably, the antibody used to capture the molecular marker is a monoclonal antibody or antibodies bound to a solid phase. Exemplary solid phase substances include, but are not limited to, microtiter plates, test tubes, magnetic, plastic or glass beads and slides. Preferably, magnetic beads coated with monoclonal antibodies (MAb) specific for epitopes of membrane-bound protein antigens are used to capture the soluble antigens.

The antibody-antigen complexes are then detected using immunoassay methods known to those skilled in the art, including sandwich immunoassays and competitive immunoassays. The antibody-antigen complexes are exposed to the same monoclonal antibodies as those used to capture the antigen, but which have been labeled with a detectable label. Suitable labels include: chemiluminescent labels, such as horseradish peroxidase; electrochemiluminescent labels, such as ruthenium and aequorin; bioluminescent labels, such as luciferase; fluorescent labels such as FITC; and enzymatic labels such as alkaline phosphatase, β-galactosidase, and horseradish peroxidase. Preferably, the label is detected by electrochemiluminescence. Most preferably, the detecting monoclonal antibody is modified by the addition of a ruthenium ($Ru^{2+}$) label.

The labeled complex is then detected using a detection technique or instrument specific for detection of the label employed. Preferably, the complexes are analyzed by an electrochemiluminescence instrument such as the ORIGEN™ ANALYZER (Igen, Inc., Gaithersburg, Md.) for $Ru^{2+}$ photon emission. Soluble antigen or antigens may also be incubated with magnetic beads coated with non-specific antibodies in an identical assay format to determine the background values of samples analyzed in the present assay.

In a preferred embodiment of the present method, solubilized antigen is complexed with monoclonal antibody-coated magnetic beads and, the beads are captured by an electromagnet present in the flow cell of the ORIGEN™ ANALYZER. After capture, the $Ru^{2+}$ present in immunocomplexes is triggered to release a photon of light by the addition of the electron donor tripropylamine followed by the application of an electrical field. Light measured by a photomultiplier tube is then expressed in electrochemiluminescent (ECL) counts. Samples positive for the parasite, such as *C. parvum*, will yield ECL counts above a set background signal.

Assay Characteristics

The detection assay described herein is efficient because of the rapid rate at which samples may be screened, processed and analyzed. Typically, samples of approximately 1 ml may be analyzed at a rate of about 60 seconds per sample. In addition, the assays of the present invention have improved efficiency due to the higher recovery of parasites as a result of limited sample processing. The detection method is a rapid and quantitative assay that is not disrupted by test sample turbidity. The assay time of the present invention for detecting *C. parvum* oocysts in source or finished water and in fecal sample is approximately six hours, while the existing microscopic assays for this organism in water samples can take up to four days to complete.

The method described herein can successfully detect *C. parvum* oocysts in one milliliter samples containing less than 50,000 oocysts, and can preferably detect as few as 10,000 oocysts/ml. Most preferably, the method can successfully detect 1,000 oocysts/ml or less. This is a significant improvement over the sensitivity of presently available methods that fail to detect *C. parvum* in one milliliter samples containing less than 50,000 oocysts.

As shown in FIGS. 1 and 2, the detection assay of the present invention is not subject to interference by sample turbidities and can properly process samples having up to 330,000 NTU. In comparison, current methodologies such as immunofluorescence assays (IFA) and enzyme immunoassays (EIA) are time consuming and severely limited by sample turbidity. Since sample turbidity is not a major impairment to successful detection by the method described herein, the assay is suitable for detecting oocysts in samples of source or finished water filtrate obtained from the eluate of filter cartridges (which commonly exhibit high turbidities as high as approximately 300,000 NTU). Furthermore, as demonstrated by FIGS. 3 and 4, the detection assay of the present invention is specific for *C. parvum*: the assay does not cross-react with other species of Cryptosporidium.

The assay is also valuable for epidemiological reasons as it may be used to identify low-level infections in patients. This is especially important because existing assays for *C. parvum* have low sensitivity making the detection of asymptomatic cryptosporidiosis a formidable task. Unlike the assay described herein, presently available assays are generally considered inaccurate and inefficient due to the variation in consistency between individual samples, the variation in amount of specimen used, and oocyst losses incurred during laborious sample preparation.

Unlike assays currently used in the art, the presently described method detects the organism by recognition of the molecular markers of the organism. The advantage of this type of recognition is that the assay is neither dependent upon recognizing the parasite in particulate form or upon detecting the presence of oocysts that are intact. Instead the assay is directed at detecting the presence of solubilized antigens that are present in abundance on oocyst cell walls. Detection based on the presence of solubilized cell wall molecular markers both increases the sensitivity of the claimed detection method, and reduces interference resulting from sample turbidity.

The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

Preparation of Solubilized *C. Parvum* Oocyst Antigens

*C. parvum* oocyst membrane-bound antigens present on the oocyst cell wall, more specifically epitopes of OW3 antigens, were solubilized in accordance with the following procedure.

Aliquots containing 500 μl of test samples, negative and positive controls containing known number of *C. parvum* oocysts (provided by Dr. M. J. Arrowood, CDC, Atlanta, Ga.), were placed in 1.7 ml siliconized microtubes and microfuged at 21,000×g for five minutes at 4° C. The supernatants were discarded and the pellets resuspended in 500 μl of solubilization buffer and incubated for 60 minutes.

When utilizing the OW3 monoclonal antibody for detecting *C. parvum* oocysts, a solubilization buffer containing 0.65% by weight Zwittergent™ 3–10 detergent (Calbiochem-Novabiochem, La Jolla, Calif.), 0.05M Tris-HCl at pH 8.0 was used to solubilize the epitopes of OW3 from the oocyst cell wall at 95° C. for 60 minutes. Following treatment, samples were microfuged at 21,000×g for 15 minutes at 4° C. A 450 μl aliquot of solubilized antigen supernatant was removed pending detection using electro-chemiluminescence (ECL).

EXAMPLE 2

Preparation of Magnetic Capture Matrix

Monoclonal antibodies including anti-OW3 antibodies and other antibodies specific for *C. parvum* oocyst wall antigens unless otherwise specified, were provided by Dr. M. J. Arrowood (CDC, Atlanta, Ga.). IgM and IgG monoclonal antibodies purified from mouse myeloma were purchased from Calbiochem-Novabiochem (La Jolla, Calif.). Also used for antigen detection were 4.5 μm M450 rat anti-mouse IgM and M450 Rat anti-mouse IgG coated magnetic beads from Dynal, Inc. (Lake Success, N.Y.). Chromatography columns including Superose-6™ media, MONO-Q™, and FAST-Desalting™ columns were purchased from Pharmacia, Biotech, Inc. (Piscataway, N.J.).

For the *C. parvum* oocyst specific assay, M450 Rat anti-mouse IgM or IgG magnetic beads were incubated at a concentration of $10^7$ beads/ml (0.075 mg/ml) with 0.001 mg/ml 45% ammonium sulfate-precipitated, chromatography-purified monoclonal antibodies specific for particular epitopes of oocyst wall antigens. For OW3 monoclonal antibodies, anti-mouse IgM magnetic beads were used in the preparation. Incubation was performed in disposable 12×75 mm borosilicate glass culture tubes and placed on an orbital shaker (approximately 800 rpm) for 60 minutes at room temperature. The beads were concentrated by placing the solution onto a magnetic rack (MPC-6 magnetic rack, Dynal, Inc., Lake Success, N.Y.) for two minutes following which the solution containing unbound monoclonal antibody was removed from the beads. Tubes were taken away from the magnet and beads were resuspended gently in 2 ml of electrochemiluminescent diluent (ECL Diluent: 0.05M Tris-HCl, 0.5M NaCl, 1% bovine serum albumin (BSA), 0.7% Tween-20, pH 8.0). Tubes were placed back on the magnetic rack, and the solution was removed as before. This wash procedure was repeated one more time. Washed beads were then resuspended in ECL diluent to a final concentration of $2.5 \times 10^6$ beads/ml (0.187 mg/ml) to yield $2.5 \times 10^5$ beads per ECL assay (0.0187 mg/100 μl/ECL assay).

EXAMPLE 3

Preparation of Ruthenium Labeled Antibodies

Chromatography purified monoclonal antibodies as described in Example 2 were conjugated to a ruthenium metal chelate TAG-NHS (an activated ruthenium label used for electrochemiluminescent detection) ester, referred to herein as the activated ruthenium label. The TAG-NHS ester used to label the detecting antibody was obtained from Igen, Inc. (Gaithersburg, Md.).

TAG-NHS was dissolved in dimethylsulfoxide (DMSO) for 15 minutes at a concentration of $1.42 \times 10^{-4}$ mM. Purified monoclonal antibodies in 0.01M $NaPO_4$ were combined with dissolved TAG at a challenge ratio of 15 to 30 moles of TAG to one mole of monoclonal antibody (no amino groups were present during reaction). For coupling ruthenium to the OW3 monoclonal antibody, a challenge ratio of 30 to 1 was used in the reaction to achieve an approximately 18 to 1 final incorporation ratio. The mixture was incubated for 60 minutes at room temperature, in the dark, on an orbital shaker. After coupling, Tris-HCl was added to a final concentration of 0.2M to stop the reaction. Unbound TAG was removed by desalting using a FAST-Desalting™ column (Pharmacia, Biotech, Inc., Piscataway, N.J.) into 0.05M Tris-HCl, 0.5M NaCl, pH 8.0. A final ruthenium to immunoglobin molar incorporation ratio for each monoclonal antibody was determined by measuring the protein concentration of the conjugate and its absorbance at 455 nm. This ratio was calculated according to reagent protocol supplied by Igen, Inc. (Gaithersburg, Md.). A 3X concentration of MAb-$Ru^{2+}$ conjugate was prepared in ECL diluent at $3 \times 10^{-4}$ mg/ml protein and was used in the assay at a final concentration of $10^{-4}$ mg/ml.

EXAMPLE 4

Electrochemiluminescent Immunoassay

Duplicate tests of each sample were performed for both *C. parvum* oocyst-specific and non-specific tests. A 100 μl aliquot of solubilized antigen supernatant, prepared as described in Example 1 above, was incubated with 100 μl of M450 Rat anti-mouse monoclonal antibody magnetic beads, prepared as described in Example 2 above, and 100 μl of $Ru^{2+}$-labeled monoclonal antibodies, prepared as described in Example 3 above, on an orbital shaker (~800 rpm) for 60 minutes at room temperature. Following incubation, samples were placed on the carousel of an ORIGEN™ ANALYZER (Igen, Inc., Gaithersburg, Md.) and assayed according to instrument specifications.

EXAMPLE 5

Determination of Number of Oocysts in Test Samples

A determination of the number of *C. parvum* oocysts detected in the test samples, as described in Example 4 above, first requires subtraction of the ECL counts of the negative sample from test samples and positive controls. ECL counts of the positive controls and test samples obtained from the non-specific assay are subtracted from the ECL counts of corresponding samples obtained from the specific assay. A standard curve is constructed using the net ECL counts obtained from the positive samples, to be used in the calculation of the number of oocysts in the test samples. For a 1 ml sample volume, ten times the calculated amount of oocyst will be present in the sample.

The following formula was used to calculate the total number of oocysts in 100 liters of water sample;

$$T = [(10N \times E)/(Q/100)] \times (100\%/R)$$

T=total number of oocysts in 100 L of water sample
N=number of oocysts/ 0.1 mL in the test sample (obtained from standard curve)

E=the total volume of the filtrate sample (mL)
Q=the total volume of the water sample collected through cartridge filter (L)

R=theoretical oocyst recovery percentage of filter cartridge used

Results of Electrochemiluminescent Assay on Test Samples Containing *C. parvum* Oocysts Different numbers of oocysts ($10^1$ to $10^6$) were spiked into the buffer or sediment samples having various nephelometric turbidity unit (NTU) values (5077 NTU, 4125 NTU and 330,000 NTU), then assayed for the presence of soluble OW3 antigen by electrochemiluminescence as described above. As shown in FIGS. 1 and 2, an increase in turbidity did not adversely affect the sensitivity or accuracy of the assay. As also shown in FIGS. 1 and 2, the assay is capable of detecting as few as 1000 oocysts per milliliter sample.

In FIGS. 3 and 4, $10^3$ to $10^5$ oocysts from various Cryptosporidium species were spiked into fecal suspension samples and assayed for the presence of solubilized OW3 antigen. The graph in FIG. 3 shows the specificity of the current method for *C. parvum*. FIG. 4 compares test results for *C. parvum* and *C. baileyi* and shows that the assay, utilizing a monoclonal antibody specific for *C. parvum*, fails to cross-react with *C. baileyi.*

Modifications and variations of the present method will be obvious to those skilled in the art from the foregoing detailed description. Such modifications and variations are intended to come within the scope of the appended claims.

We claim:

1. A method for detecting Cryptosporidium in a sample comprising:

(a) incubating the sample with a buffered solution comprising a synthetic zwitterionic compound, wherein the incubation is at a temperature of greater than 75° C. for a sufficient amount of time to result in a protein or a glycoprotein antigen of a Cryptosporidium oocyst being solubilized in the buffered solution, (b) reacting the antigen of the Cryptosporidium oocyst in the buffered solution with an antibody that specifically binds the solubilized antigen to form an antibody-antigent complex; and (c) detecting the antibody-antigen complex in the buffered solution by an immunoassay method, wherein the detection of the antigen-antibody complex indicates the presence of Cryptosporidium in the sample.

2. The method of claim 1, wherein the protein or glycoprotein is a membrane-bound protein or glycoprotein of an oocyst wall of the Cryptosporidium.

3. The method of claim 1, wherein the sample contains less than 50,000 oocysts/ml.

4. The method of claim 1, wherein the Cryptosporidium is Cryptosporidium parvum.

5. The method of claim 1, wherein the antibody is bound to a solid phase.

6. The method of claim 1, wherein the detection is by electrochemiluminescence.

7. The method of claim 1, further comprising incubating the antibody-antigen complex with a second antibody specifically binds the antigen or the antibody-antigen complex, wherein the second antibody is labeled with a detectable label.

8. The method of claim 7, wherein the label is selected from the group consisting of an electrochemiluminescent label, a chemiluminescent label, an enzymatic label, a bioluminescent label, and a fluorescent label.

9. The method of claim 8, wherein the electrochemiluminescent label is selected from the group consisting of ruthenium and aequorin.

10. The method of claim 1, wherein the antigen is an epitope of the OW3 antigen of the *Cryptosporidium parvum* oocyst.

11. The method of claim 1, wherein the sample is incubated with the buffered solution comprising the compound for at least 30 minutes.

12. The method of claim 1, wherein the sample is a water sample.

13. The method of claim 12, wherein the water sample is selected from the group consisting of natural bodies of water, community water reserviors, and recreational waters, wherein the recreational waters are selected from the group consisting of swimming pools, whirlpools, hot tubs, spas, water parks, naturally occurring fresh waters, and marine surface waters.

14. The method of claim 1, wherein the sample is a biological sample.

15. The method of claim 14, wherein the sample is a fecal sample.

16. An assay kit for the detection of Cryptosporidium in a sample comprising, (a) an antibody specific for a solubilized Cryptosporidium oocyst antigen wherein the antigen is a protein or glycoprotein, and (b) a buffered solution comprising a compound selected from the group consisting of n-Hexadecyl-N,N-dimethyl-3-ammonio-1-propanesulfonate, n-Octyl-N,N-dimethyl-3-ammonio-1-propanesulfonate, n-Decyl-N,N-dimethyl-3-ammonio-1propanesulfonate, n-Dodecyl-N,N-dimethyl-3-ammonio-1-propanesulfonate, n-Tetradecyl-N,N-dimethyl-3-ammonio-1-propanesulfonate, wherein the buffered solution solubilizes the Cryptosporidium oocyst antigen present in the sample.

17. The assay kit of claim 16, wherein the antibody is immobilized on a solid phase.

18. The assay kit of claim 16, further comprising a labeled antibody that specifically binds the solubilized antigen.

19. The method of claim 1, wherein the sample is a turbid water sample.

20. The assay kit of claim 16, wherein the sample is a turbid water sample.

21. The method of claim 1, wherein the sample contains less than 10,000 oocysts/ml.

22. The method of claim 1, wherein the sample contains less than 1,000 oocysts/ml.

23. The method of claim 1, wherein the antibody is a monoclonal antibody.

24. The method of claim 1, wherein the sample has a turbidity of up to 300,000 NTU.

25. The method of claim 1, wherein the buffered solution has a pH of less than pH=7 and greater than pH=4.

26. The method of claim 1, wherein the buffered solution has a pH of greater than pH=7 and less than pH=10.

27. The method of claim 1, wherein the compound is selected from the group consisting of n-Hexadecyl-N,N-dimethyl-3-ammonio-1-propanesulfonate,n-Octyl-N,N-dimethyl-3-ammonio-1-propanesulfonate, n-Decyl-N,N-dimethyl-3-ammonio-1-propanesulfonate,n-Dodecyl-N,N-dimethyl-3-ammonio-1-propanesulfonate and n-tetradecyl-N,N-dimethyl-3-ammonio-1-propanesulfonate.

28. The method of claim 1, wherein the detecting is not by microscopy.

* * * * *